United States Patent [19]

Haluska

[11] Patent Number: 5,446,088
[45] Date of Patent: Aug. 29, 1995

[54] PRECURSOR FOR CERAMIC COATINGS

[75] Inventor: Loren A. Haluska, Midland, Mich.

[73] Assignee: Dow Corning Corporation, Midland, Mich.

[21] Appl. No.: 270,531

[22] Filed: Jul. 5, 1994

Related U.S. Application Data

[63] Continuation of Ser. No. 62,621, May 17, 1993, abandoned.

[51] Int. Cl.$^6$ .............................................. C08G 77/12
[52] U.S. Cl. ...................... 524/588; 524/858; 528/39; 528/31; 528/8; 528/9; 528/15; 106/287.12; 106/287.16
[58] Field of Search ................ 528/39, 31, 15, 8, 9; 524/858, 588; 106/287.12, 287.16

[56] References Cited

U.S. PATENT DOCUMENTS

| | | | |
|---|---|---|---|
| 3,489,782 | 1/1970 | Pruvost et al. | 528/39 |
| 3,624,030 | 11/1971 | Pruvost et al. | 528/39 |
| 3,811,918 | 5/1974 | Levene | 117/47 H |
| 4,395,563 | 7/1983 | Hayes | 556/459 |
| 4,999,397 | 3/1991 | Weiss et al. | 524/755 |

OTHER PUBLICATIONS

*Organosilicon Heteropolymers and Heterocompounds,* Rochow ed. pp. 267, 302, 303, 405, 444, 445 1970.
*Chemistry and Technology of Silicones,* Noll pp. 94, 95 1968.
R. Muller, Technical Use Of Hydrolysis And Condensation Products Of Inorganic Halosilanes, Chem. Tech., 2, 7-13, 41-9 (1950).
C. Eaborn, Organosilicon Compounds, Butterworths Scientific Publications, 1960, pp. 301-311.

*Primary Examiner*—John C. Bleutge
*Assistant Examiner*—Margaret W. Glass
*Attorney, Agent, or Firm*—Roger E. Gobrogge

[57] ABSTRACT

A method of co-hydrolyzing silanes of the formulas HSi(OR)$_3$ and Si(OR)$_4$ to form a soluble resinous co-hydrolysate is disclosed. The method comprises hydrolyzing the silanes with water in an acidified oxygen containing polar organic solvent. The invention also relates to the soluble co-hydrolysates formed thereby as well as the method of using the co-hydrolysates to provide coatings on various substrates, including electronic devices.

8 Claims, No Drawings

PRECURSOR FOR CERAMIC COATINGS

This is a continuation of application Ser. No. 08/062,621 filed on May 17, 1993, now abandoned.

BACKGROUND OF THE INVENTION

This invention relates to a method for co-hydrolyzing silanes of the formulas $HSi(OR)_3$ and $Si(OR)_4$ to form soluble resinous co-hydrolysates. The invention also relates to the soluble co-hydrolysates formed thereby as well as the method of using said co-hydrolysates to provide coatings on various substrates, including electronic devices.

It is known in the prior art that organotrialkoxysilanes dissolved in a solvent are readily hydrolyzed by water in an acidic environment. See, for example, Eaborn, "Organosilicon Compounds", Butterworth's Scientific Publications, London (1960) p 301. The resultant hydrolysates, however, can be unstable and often condense upon formation to yield insoluble organopolysiloxane gels.

Similar hydrolysis and condensation reactions are also known to occur in hydridosilanes (silanes with an Si-H bond) with organoxy functional groups. The Si-H bonds of these silanes, however, are susceptible to cleavage resulting in the production of insoluble gels. For instance, Muller in Chem Tech 2, 7-13, 41-49 (1950) teaches that the hydrolysis of triethoxysilane to silanetriol in an alcohol results in the production of an insoluble gel.

Levene in U.S. Pat. No. 3,811,918 teaches the formation of a gel resistant glass precursor composition which may be heated to form a protective glass coating. The coating composition is formed by a partially hydrolyzing a silicon alkoxide in a solvent, reacting the partial hydrolysate with an aqueous solution of a metal oxide forming compound, hydrolyzing this solution with additional water and then adding an acid to form a stable, gel-free solution. The reference, however, does not disclose co-hydrolyzing silanes.

Hayes in U.S. Pat. No. 4,395,563 teaches a method of hydrolyzing an alkoxysilane in which the alkoxysilane is mixed with a stoichiometric excess of water and an acid catalyst. The resultant hydrolysis mixture is then neutralized and the hydrolysis products separated. Again, however, this reference fails to teach co-hydrolysis of silanes.

It has now been unexpectedly found that the process of the present invention provides a method for co-hydrolyzing silanes to form soluble resins which may be used to form coatings.

SUMMARY OF THE INVENTION

This invention relates to a method of co-hydrolyzing silanes of the formula $HSi(OR)_3$ and $Si(OR)_4$ to form a soluble resinous co-hydrolysate. R in these formulas is independently an organic group which, when bonded to silicon through the oxygen atom, forms a hydrolyzable substituent. The method comprises first mixing the silanes, an oxygen containing polar organic solvent, water and an acid. Hydrolysis of this mixture is then facilitated for a time sufficient to hydrolyze or partially hydrolyze the silanes.

The invention also relates to soluble resinous co-hydrolysate polymers having units of the formula $HSi(OH)_x(OR)_yO_{z/2}$ and $Si(OH)_a(OR)_bO_{c/2}$, wherein each R is independently an organic group which, when bonded to silicon through the oxygen atom, forms a hydrolyzable substituent, $x=0-2$, $y=0-2$, $z=1-3$, $x+y+z=3$, $a=0-3$, $b=0-3$, $c=1-4$ and $a+b+c=4$.

The invention is also related to a method of forming a coating on a substrate in which the substrate is coated with the above hydrolysate and the coated substrate then heated to a temperature of between about 50° and about 1000° C.

DETAILED DESCRIPTION OF THE INVENTION

The instant invention relates to a method of co-hydrolyzing silanes of the formulas $HSi(OR)_3$ and $Si(OR)_4$ and to the co-hydrolysates formed thereby. These co-hydrolysates are particularly valuable in the formation of coatings.

The silanes co-hydrolyzed in the process of the present invention have the formulas $HSi(OR)_3$ and $Si(OR)_4$. R in this formula can be any organic group which, when bonded to silicon through the oxygen atom, forms a hydrolyzable substituent. Generally, these organic groups contain 1-20 carbon atoms. As such, examples of the hydrolyzable substituents include alkoxy such as methoxy, ethoxy, propoxy, butoxy, or hexoxy; alkenoxy such as ethenoxy or propenoxy; cycloalkoxy such as cyclopentoxy or cyclohexoxy; aryloxy such as phenoxy; cycloalkenyloxy such as cyclopentoxy; and acyloxy such as acetoxy. The preferred silanes contain alkoxy substituents with 1-6 carbon atoms and the most preferred silanes have methoxy and/or ethoxy substituents.

The percentage of each silane can be varied over a wide range depending on the desired product. For instance, the mole percent of $HSi(OR)_3$ to $Si(OR)_4$ can vary from about 1/1000 to 1000/1 with a range of from about 1/100 to 100/1 being most preferred. It has been discovered, however, that the shelf life of the resultant material is often longer when this ratio is less than about 3/1.

When the above silanes are subjected to the co-hydrolysis conditions described herein, the hydrolyzable substituents are at least partially replaced with hydroxyl groups and/or Si-O-Si linkages. The novelty of this invention resides in the fact that said hydrolysis occurs without cleavage of the Si-H bond and, thus, results in a soluble product.

The above silanes are hydrolyzed in a mixture comprising an oxygen containing polar organic solvent, water and an acid. The oxygen containing polar organic solvent utilized herein is one which is capable of dissolving the silanes and promoting hydrolysis. Generally, the solvent is a base which is capable of hydrogen bonding with the resultant co-hydrolysate for stability. Examples of suitable solvents include alcohols such as methanol, ethanol, isopropanol or butanol, polyols such as glycols, ethers such as ethyl ether, tetrahydrofuran or dioxane, ketones such as acetone or methyl ethyl ketone, esters such as methyl acetate or glycol ethers such as the monomethyl ether of ethylene glycol or the monomethyl ether of propylene glycol. In addition, the above solvents may also be mixed with various other miscible solvents such as toluene or xylene. The preferred solvents herein are alcohols such as ethanol, isopropanol, butanol or mixtures thereof.

The solvent or solvents are generally used in an amount which dilutes the silanes to between about 1 and about 50 weight percent solids, preferably 5-25 weight percent solids. The entire amount of solvent may be included in the hydrolysis mixture or, alternatively, the silanes may be diluted for hydrolysis and then the resultant hydrolysate further diluted to provide additional stability.

Water is also included in the hydrolysis mixture in an amount effective to hydrolyze or partially hydrolyze the silanes. The stoichiometric amount of water necessary for complete hydrolysis can be calculated in the following manner: 1 mole of water hydrolyses $\frac{2}{3}$ mole of $HSi(OR)_3$ or $\frac{1}{2}$ mole $Si(OR)_4$ by the following reactions:

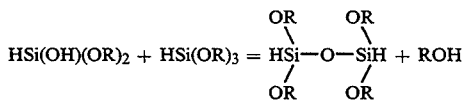

and

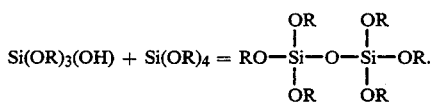

Therefore, 1.5 moles of water are needed to completely hydrolyze every mole of $HSi(OR)_3$ and 2 moles of water are needed to completely hydrolyze every mole of $Si(OR)_4$.

Generally the stability of the hydrolysate is increased when the amount of water is limited (i.e., partial hydrolysates are formed). Therefore, it is generally preferred to use less than a stoichiometric amount of water (i.e., an amount of water less than that necessary for complete hydrolysis).

An acid or mixture of acids are also included in the hydrolysis mixture to both catalyze the hydrolysis reaction and stabilize the hydrolyzate once formed. Generally, most inorganic acids and some organics will function herein. Examples of suitable agents include the hydrogen halides such as HCl or HF, nitric, sulfuric, or carboxylic acids such as acetic. They may be utilized in a concentrated or dilute form in an amount which will acidify the reaction medium (i.e., create a pH less than 7). Generally, amounts of greater than about 0.1 weight percent based on the weight of the mixture of a 5% aqueous acid solution will be effective with greater than about 0.4 weight percent of said dilute solution being more preferred.

Once the appropriate amounts of reactants have been calculated, they are combined to form a hydrolysis mixture. Although any order of mixing the reactants can be used, generally the silanes are dissolved in the solvent and then the acid and water added to the solution.

Some hydrolysis usually occurs when the above components are combined. To increase the rate and extent of reaction, however, various facilitating measures such as temperature control and/or stirring are utilized. For example, stirring the mixture with the application of mild heat in the range of 40°–100° C. for 0.1–24 hours will generally produce a desirable hydrolysate.

In addition to the silanes, modifying ceramic oxide precursors may also be included in the above mixture and cohydrolyzed to a hydrolysate. Examples of such ceramic oxide precursors include compounds of various metals such as aluminum, titanium, zirconium, tantalum, niobium and/or vanadium as well as various non-metallic compounds such as those of boron or phosphorous which may be dissolved in solution, hydrolyzed, and subsequently pyrolyzed, at relatively low temperatures and relatively rapid reaction rates to form ceramic oxide coatings.

The above ceramic oxide precursor compounds generally have one or more hydrolyzable groups bonded to the above metal or non-metal, depending on the valence of the metal. The number of hydrolyzable groups to be included in these compounds is not critical as long as the compound is soluble in the solvent. Likewise, selection of the exact hydrolyzable substituent is not critical since the substituents are either hydrolyzed or pyrolyzed out of the system. Typical hydrolyzable groups include, but are not limited to, alkoxy, such as methoxy, propoxy, butoxy and hexoxy, acyloxy, such as acetoxy, or other organic groups bonded to said metal or non-metal through an oxygen such as acetylacetonate. Specific compounds, therefore, include zirconium tetracetylacetonate, titanium dibutoxy diacetylacetonate, aluminum triacetylacetonate and tetraisobutoxy titanium. The modifying ceramic oxide precursor is generally present in an amount such that the final ceramic coating contains 0.1 to 30% modifying ceramic oxide.

In the case of highly reactive modifying ceramic oxide precursors which contain substituents such as propoxides, isopropoxides, butoxides, isobutoxides or acetylacetonates, the modifying ceramic oxide precursors and silanes can be premixed and heated to reflux in ethanol for 24 hours to afford a homogenous reaction mixture which can be hydrolyzed uniformly and at a controlled rate. However, attempts to pre-hydrolyze a mixture of the above mentioned highly reactive modifying ceramic oxide precursors and silanes without the condensation reaction results in preferential and rapid hydrolysis of the modifying ceramic oxide precursor over that of the silanes, resulting in rapid, non-homogenous gelation of the reaction mixture.

An alternative method of cohydrolyzing the reactive modifying ceramic oxide precursors would be to hydrolyze the silanes as disclosed supra, followed by adding the reactive modifying ceramic oxide precursor and less than or equal to a stoichiometric amount of water for hydrolyzing said modifying ceramic oxide precursor to the hydrolysate solution. When the hydrolysis of this mixture is facilitated as discussed supra, a uniform, soluble hydrolysate results.

The above co-hydrolysates may also be catalyzed by the addition of a platinum or rhodium catalyst which assists in increasing the rate and extent of ceramification on pyrolysis. Any platinum or rhodium compound or complex which can be solubilized in this mixture will be operable. For instance, an organoplatinum composition such as platinum acetylacetonate or rhodium catalyst $RhCl_3[S(CH_2CH_2CH_2CH_3)_2]_3$, obtained from Dow Corning Corporation, Midland, Mich. are all within the scope of this invention. The above catalysts are generally added to the solution in an amount of between about 1 to 1000 ppm platinum or rhodium based on the weight of resin in solution.

During the formation of the hydrolysate, partial condensation is likely to spontaneously occur. The resultant resinous hydrolysate, therefore, is a polymer containing units of the formula:

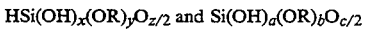

$HSi(OH)_x(OR)_yO_{z/2}$ and $Si(OH)_a(OR)_bO_{c/2}$ wherein R is as defined for the silane, $x=0-2$, $y=0-2$, $z=1-3$, $x+y+z=3$, $a=0-3$, $b=0-3$, $c=1-4$ and a+b+c=4. The resin is soluble in the acidified solvents disclosed herein and its stability contingent primarily on the degree of hydrolysis and condensation.

The above resins can be used to form coatings on substrates. The method of forming such coatings generally comprises applying a solution of the resin to the surface of a substrate and then pyrolyzing the coated substrate. The method of coating substrates can be, but is not limited to, spin coating, dip coating, spray coating or flow coating. Other equivalent means, however, are also deemed to be within the scope of this invention.

The solvent in the coating solution is then allowed to evaporate from the coated substrate resulting in the deposition of a preceramic resin coating. Any suitable means of evaporation may be used such as simple air drying by exposure to an ambient environment, by the application of a vacuum or mild heat (eg., less than 50° C.) or during the early stages of the heat treatment. It is to be noted that when spin coating is used, the additional drying period is minimized as the spinning drives off the solvent.

Once the coating is applied, it is then heated to a temperatures in the range of about 50° C. to about 1000° C., depending on the pyrolysis environment. Such environments can include, for example, air, oxygen, oxygen plasma, inert gases, water vapor (eg., steam), ammonia, amines, other oxidizing gases such as nitrous oxide, and the like.

Such heating is generally continued for a time sufficient to convert the resin to silica. Time periods in the range of a few minutes for very thin films to several hours for very thick films, depending on the temperature, are generally useful herein. It is particularly preferred to heat the coated substrates at a temperature of about 100°-600° C. for up to about 6 hours.

Any method of heating such as the use of a quartz tube furnace, a convection oven, or radiant or microwave energy is generally functional herein. Similarly, the rate of heating is generally not a critical factor, but it is most practical and preferred to heat the substrate as rapidly as possible.

Upon heating, these hydrolysates are converted to smooth layers of amorphous silica. These layers have found particular utility in coating electronic circuits wherein they may serve as a protective planarizing coating to preserve the integrity of the circuits against environmental stress or they may function as a dielectric for use in multilayered devices. They may be applied directly on the circuit surface or they may be applied on a primary passivated circuit surface to seal the bond pads, pinholes and cracks of the primary passivation. These coatings also provide an adherent surface for subsequently applied coatings. Such subsequent coatings include, for example, additional passivating and/or barrier layers as described in U.S. Pat. No. 4,753,855 which is incorporated herein in its entirety.

The following nonlimiting examples are provided so that one skilled in the art may more fully understand the invention.

EXAMPLE 1

A mixture was prepared by combining 2.738 g of HSi(OEt)$_3$, 3.471 g of Si(OEt)$_4$, 8.951 g of isopropyl alcohol, and 0.840 g of water containing 3 drops of 5% aqueous HCl. The mixture was stirred and heated to 60°-70° C. for 45 minutes and then allowed to cool. To the resultant mixture was added 4.0 g butanol.

The above mixture was spin coated on a 1" silicon wafer at 3000 RPM for 35 seconds. The coated wafer was heated at 450° C. for 3 hours in ammonia and ammonium hydroxide vapor. The FTIR spectra on the silicon wafer showed the typical Si-O-Si band at 1062 cm$^{-1}$ and the absence of the Si-H band at 2245 cm$^{-1}$ and the SiOH band at 3200- 3700 cm$^{-1}$. The coating was 0.6483 micrometers thick and the refractive index was 1.427 (8300 gamma).

EXAMPLE 2

A mixture was prepared by combining 4.105 g of HSi(OEt)$_3$, 1.735 g of Si(OEt)$_4$, 9.321 g of isopropyl alcohol, and 0.840 g of water containing 3 drops of 5% aqueous HCl. The mixture was stirred and heated to 60°-70° C. for 45 minutes and then allowed to cool. To the resultant mixture was added 4.0 g butanol.

The above mixture was spin coated on a 1" silicon wafer at 3000 RPM for 35 seconds. The coated wafer was heated at 450° C. for 3 hours in ammonia and ammonium hydroxide vapor. The FTIR spectra on the silicon wafer showed the typical Si-O-Si band at 1062cm $^{-1}$, the absence of the Si-H band at 2245 cm$^{-1}$ and a trace of SiOH. The coating was 0.6801 micrometers and the refractive index was 1.405 (8300 gamma).

EXAMPLE 3

A mixture was prepared by combining 4.927 g of HSi(OEt)$_3$, 0.695 g of Si(OEt)$_4$, 9.539 g of isopropyl alcohol, and 0.840 g of water containing 3 drops of 5% aqueous HCl. The mixture was stirred and heated to 60°-70° C. for 45 minutes and then allowed to cool. To the resultant mixture was added 4.0 g butanol.

The above mixture was spin coated on a 1" silicon wafer at 3000 RPM for 35 seconds. The coated wafer was heated at 450° C. for 3 hours in ammonia and ammonium hydroxide vapor. The FTIR spectra on the silicon wafer showed the typical Si-O-Si band at 1062cm $^{-1}$, the absence of the Si-H band at 2245 cm$^{-1}$ and a trace of SiOH. The coating was 0.6269 micrometers thick and the refractive index was 1.418 (8300 gamma).

EXAMPLE 4

A mixture was prepared by combining 1.368 g of HSi(OEt)$_3$, 5.206 g of Si(OEt)$_4$, 8.587 g of isopropyl alcohol, and 0.898 g of water containing 3 drops of 5% aqueous HCl. The mixture was stirred and heated to 60°-70° C. for 45 minutes and then allowed to cool. To the resultant mixture was added 4.0 g butanol.

The above mixture was spin coated on a 1" silicon wafer at 3000 RPM for 35 seconds. The coated wafer was heated at 450° C. for 3 hours in ammonium hydroxide vapor. The FTIR spectra on the silicon wafer showed the typical Si-O-Si band at 1062 cm$^{-1}$, the absence of the Si-H band at 2245cm $^{-1}$ and a trace of SiOH. The coating was 0.6443 micrometers and the refractive index was 1.418 (8300 gamma).

TABLE 1

| Ex No | Mole Ratio HSi(OEt)$_3$/Si(OR)$_4$ | Percent Hydrolyzed | Shelf Life |
|---|---|---|---|
| 2 | 3/1 | 86 | 2 weeks |
| 3 | 9/1 | 90 | 1 week |
| 4 | 1/3 | 80 | 7 months |

TABLE 1-continued

| | Shelf Life | | |
|---|---|---|---|
| Ex No | Mole Ratio $HSi(OEt)_3/Si(OR)_4$ | Percent Hydrolyzed | Shelf Life |
| C* | 1/0 | 90 | 1 week |

C* - control - only triethoxysilane hydrolyzed

That which is claimed is:

1. A stable mixture comprising an acidified oxygen-containing polar organic solvent and a soluble resinous co-hydrolysate comprising a polymer having units of the formula $HSi(OH)_x(OR)_yO_{z/2}$ and $Si(OH)_a(OR)_bO_{c/2}$, wherein each R is independently an organic group which, when bonded to silicon through the oxygen atom, forms a hydrolyzable substituent, $x=0-2$, $y=0-2$, $z=1-3$, $x+y+z=3$, $a=0-3$, $b=0-3$, $c=1-4$, $a+b+c=4$ and the ratio of $HSi(OH)_x(OR)_yO_{z/2}$ units to $Si(OH)_a(OR)_bO_{c/2}$ units is 1:3 or less.

2. The mixture of claim 1 wherein R is an alkyl of 1-6 carbon atoms.

3. The mixture of claim 1 wherein the solvent is present in an amount such that the co-hydrolysate is diluted to between about 1 and about 50 weight percent solids.

4. The mixture of claim 1 wherein a platinum or rhodium catalyst is additionally present.

5. A stable mixture comprising an acidified oxygen-containing polar organic solvent and a soluble resinous co-hydrolysate comprising a polymer having units of the formula $HSi(OH)_x(OR)_yO_{z/2}$ and $Si(OH)_a(OR)_bO_{c/2}$ and modifying ceramic oxide units, wherein each R is independently an organic group which, when bonded to silicon through the oxygen atom, forms a hydrolyzable substituent, $x=0-2$, $y=0-2$, $z=1-3$, $x+y+z=3$, $a=0-3$, $b=0-3$, $c=1-4$, $a+b+c=4$, the modifying ceramic oxide unit is the condensed hydrolysate of a modifying ceramic oxide precursor comprising an element selected from the group consisting of titanium, zirconium, aluminum, tantalum, vanadium, niobium, boron and phosphorous with at least one hydrolyzable substituent selected from the group consisting of alkoxy or acyloxy, and the ratio of $HSi(OH)_x(OR)_yO_{z/2}$ units to $Si(OH)_a(OR)_bO_{c/2}$ units is 1:3 or less.

6. The mixture of claim 5 wherein R is an alkyl of 1-6 carbon atoms.

7. The mixture of claim 5 wherein the solvent is present in an amount such that the co-hydrolysate is diluted to between about 1 and about 50 weight percent solids.

8. The mixture of claim 5 wherein a platinum or rhodium catalyst is additionally present.

* * * * *